(12) United States Patent
Lehman et al.

(10) Patent No.: US 9,677,991 B2
(45) Date of Patent: Jun. 13, 2017

(54) SAND AND DUST ENVIRONMENTAL TESTING SYSTEM

(71) Applicant: Air Dynamics Industrial Systems Corporation, York, PA (US)

(72) Inventors: Daniel P. Lehman, York, PA (US); Daniel A. Lehman, York, PA (US)

(73) Assignee: Air Dynamics Industrial Systems Corporation, York, PA (US)

( * ) Notice: Subject to any disclaimer, the term of this patent is extended or adjusted under 35 U.S.C. 154(b) by 221 days.

(21) Appl. No.: 14/253,643

(22) Filed: Apr. 15, 2014

(65) Prior Publication Data

US 2014/0338470 A1 Nov. 20, 2014

Related U.S. Application Data

(62) Division of application No. 12/958,132, filed on Dec. 1, 2010, now Pat. No. 8,733,186.

(60) Provisional application No. 61/266,052, filed on Dec. 2, 2009.

(51) Int. Cl.
*G01N 17/00* (2006.01)
*G01M 99/00* (2011.01)
*G01N 17/02* (2006.01)

(52) U.S. Cl.
CPC ........ *G01N 17/002* (2013.01); *G01M 99/002* (2013.01); *G01N 17/02* (2013.01)

(58) Field of Classification Search
CPC .... G01N 17/00; G01N 17/002; G01M 99/002
USPC ....................................... 73/865.6
See application file for complete search history.

(56) References Cited

U.S. PATENT DOCUMENTS

| 2,346,690 | A | * | 4/1944 | Larkins, Jr. | 222/161 |
| 2,703,488 | A | * | 3/1955 | Gevantman | G01N 17/00 73/147 |
| 4,646,564 | A | * | 3/1987 | Ide | G09B 23/12 73/147 |
| 5,381,701 | A | * | 1/1995 | Frankenthal | G01R 31/2849 73/865.6 |
| 5,615,830 | A | * | 4/1997 | Matsunaga | B05B 5/1683 222/368 |

(Continued)

FOREIGN PATENT DOCUMENTS

JP 56-147040 * 11/1981

*Primary Examiner* — Daniel S Larkin
(74) *Attorney, Agent, or Firm* — PatentBest; Andrew McAleavey (57) ABSTRACT

An environmental testing system for environmental testing with particulate matter, such as sand and dust, is disclosed. The testing system uses a feeder to feed precise amounts of particulate matter into an injector, which injects the particulate matter into the airflow leading to a test chamber with approximately the same velocity as the surrounding airflow. The feeder may be a loss-in-weight gravimetric feeder, and the injector may be a Venturi valve actuated by compressed air. The system also includes operator protection features, such as an exhaust fan that creates negative pressure when the door to the test chamber is opened, and when particulate matter is dumped into the system. A temperature control system heats and cools the airflow during tests, a pneumatic conveying system moves fluidized particulate matter into and out of the system, and a controller provides automatic control over the system.

5 Claims, 9 Drawing Sheets

(56) References Cited

U.S. PATENT DOCUMENTS

| | | | | |
|---|---|---|---|---|
| 6,360,621 | B1 * | 3/2002 | Eldred | G01N 17/002 |
| | | | | 73/865.6 |
| 7,127,958 | B2 * | 10/2006 | Blewett | G01M 17/007 |
| | | | | 73/865.6 |
| 7,363,831 | B2 * | 4/2008 | Willemin | G01N 17/00 |
| | | | | 73/865.6 |
| 2010/0080261 | A1 * | 4/2010 | Lee | G01N 3/60 |
| | | | | 374/57 |

* cited by examiner

SAND AND DUST ENVIRONMENTAL TESTING SYSTEM

CROSS-REFERENCE TO RELATED APPLICATIONS

This patent application is a divisional of U.S. patent application Ser. No. 12/958,132, filed Dec. 1, 2010, now U.S. Pat. No. 8,733,186, which claims priority to U.S. Provisional Patent Application No. 61/266,052, filed Dec. 2, 2009. The contents of both of those applications are incorporated by reference herein in their entirety.

BACKGROUND OF THE INVENTION

1. Field of the Invention

The invention relates to environmental testing systems, and more particularly, to environmental testing systems capable of exposing a test piece to sand and dust.

2. Description of Related Art

Many pieces of equipment are subjected to environmental extremes during their service lifetimes. Those environmental extremes may be, for example, extremes of temperature, pressure, vibration, acceleration, or shock. Equipment may also be subjected to environmental conditions such as rain, wind, sand, dust, and humidity, to name a few. These environmental conditions can shorten the operational lifetime of a piece of equipment or cause it to fail entirely.

Over time, various methods have evolved for testing equipment to determine whether it can withstand various environmental extremes and conditions, and if so, what effect those extremes might have on the equipment. Most of these methods involve placing the equipment in question in an environmental test chamber that is equipped to simulate the desired environmental extremes.

Environmental testing techniques and methods are used widely in industry, both to certify that equipment will not fail under particular conditions and to evaluate the nature and reproducibility of failures that do occur. However, because resistance to environmental extremes is particularly important in the case of military equipment, a number of military organizations have produced standards documents that define how different types of environmental tests are to be performed. In the United States, MIL-STD-810G, "Department of Defense Test Method Standard for Environmental Engineering Considerations and Laboratory Tests" contains military standards for a variety of different types of environmental testing. Among the methods covered by MIL-STD-810G are methods for sand and dust environmental testing.

In a typical sand or dust environmental test, a piece of equipment is placed in a test chamber, and the test chamber is heated to an elevated temperature, e.g. 180° F. (82° C.). Either sand or dust is blown into the chamber continuously for the duration of the test, which typically lasts about ninety minutes.

Test systems for performing sand or dust environmental testing do exist, but these systems do have a number of difficulties. First and foremost, these systems can have difficulty producing a laminar airflow into the environmental testing chamber that has an even distribution of dust or sand particles, all of which are moving at essentially the same velocity. Moreover, in some of these systems, the air mover or blower that creates the airflow into the test chamber is directly exposed to the sand or dust, which can cause wear and reduce the effectiveness of the blower.

Finally, sand and dust may be hazardous to human health. Sand in particular can cause silicosis, a serious lung condition, if it is inhaled. For that reason, it is important to protect the operator of a sand and dust environmental testing system from exposure to the sand and dust.

SUMMARY OF THE INVENTION

One aspect of the invention relates to an environmental testing system. The environmental testing system is designed for environmental tests that expose test pieces to particulate matter, typically either sand or dust, entrained in an airflow. In the environmental testing system, a blower creates the airflow that recirculates through the system. The blower is arranged relative to a filter chamber such that it is on the "clean" side of the system and is not exposed to the particulate matter. The system also has a particulate matter feed mechanism that includes a feeder that feeds measured amounts of particulate matter to an injector, which injects the particulate matter into an inlet duct with a velocity that at least substantially matches the velocity of a surrounding airflow in the inlet duct. The inlet duct is connected to the inlet of an environmental test chamber. In some embodiments, the feeder may be a loss-in-weight gravimetric feeder, and the injector may be a Venturi valve.

Another aspect of the invention relates to operator protection systems for an environmental testing system. In a system according to this aspect of the invention, the environmental test chamber includes an outlet that is coupled to an exhaust fan and filter elements. The exhaust fan may also be coupled to a particulate matter input station, where particulate matter is introduced into the system. When the door of the environmental test chamber is opened, or when particulate matter is introduced into the system, the exhaust fan is activated to create a negative pressure, drawing any particulate matter away from the user.

Yet another aspect of the invention relates to material handling and conveying systems for environmental testing systems. In environmental testing systems according to this aspect of the invention, a pneumatic conveying system, including a pump and a network of pipes, are used to convey fluidized particulate matter into the system. A series of gates or valves are provided in the network of pipes such that the same pneumatic system can be used to collect used particulate matter and direct it in fluidized form either back to the feed system for re-use or to a waste hopper for disposal.

Additional aspects of the invention pertain to methods of controlling particulate matter environmental testing systems to maintain particular temperatures and other test conditions during an environmental test.

These and other aspects, features, and advantages of the invention will be set forth in the description that follows.

BRIEF DESCRIPTION OF THE DRAWING FIGURES

The invention will be described with respect to the following drawing figures, in which like numerals represent like features throughout the drawings, and in which.

DETAILED DESCRIPTION

Figure 1:
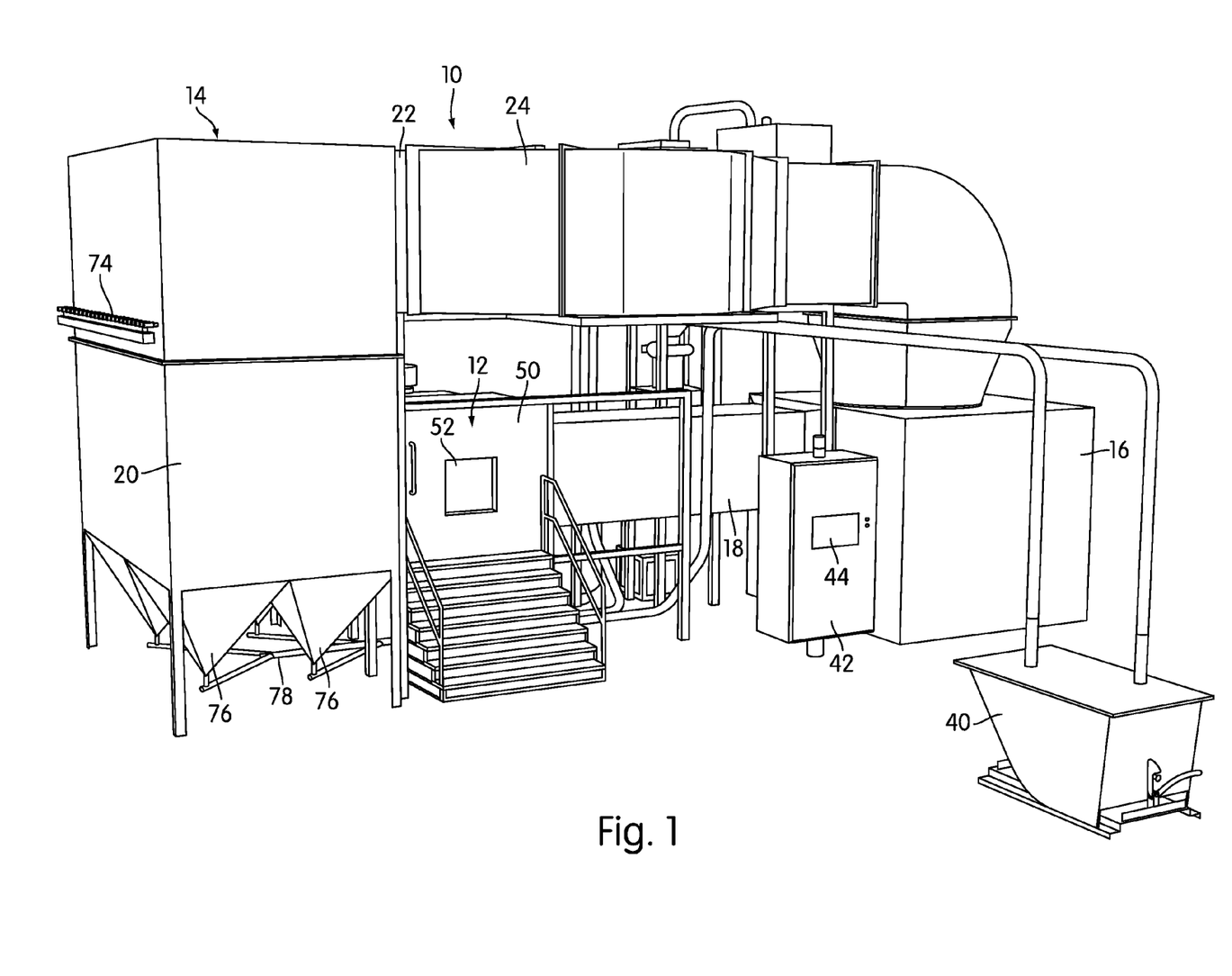
FIG. 1 is a front perspective view of a sand and dust environmental testing system according to one embodiment of the invention.

FIG. 1 is a front perspective view of a sand and dust environmental test system, generally indicated at 10, according to one embodiment of the invention. The testing system 10 is designed to expose a test piece to high-velocity airstreams with entrained sand or dust at elevated temperatures, in order to determine what effect those conditions have on the test piece. The testing system 10 may be constructed to perform tests according to recognized standards, such as the test methods set forth in MIL-STD-810G, although that need not necessarily be the case.

The testing system 10 includes an environmental chamber 12 into which the test piece (not shown in FIG. 1) is placed for testing. An air handling system, generally indicated at 14, creates the airflow necessary for the test, filters the particulate matter out of the air, and recirculates the air continuously during the test. The air handling system 14 comprises, among other components, a blower housing 16, where the blower or air mover is located; a delivery duct 18 that leads into the environmental test chamber 12 and into which the sand or dust is injected as the airstream flows past; a filter chamber 20, where the sand or dust is filtered from the airstream; and a set of upper ducts 22, 24, which direct the filtered air back toward the blower housing 16 and also contain a temperature control system. The temperature control system and methods of heating and cooling the air will be described below in more detail.

Figure 2:
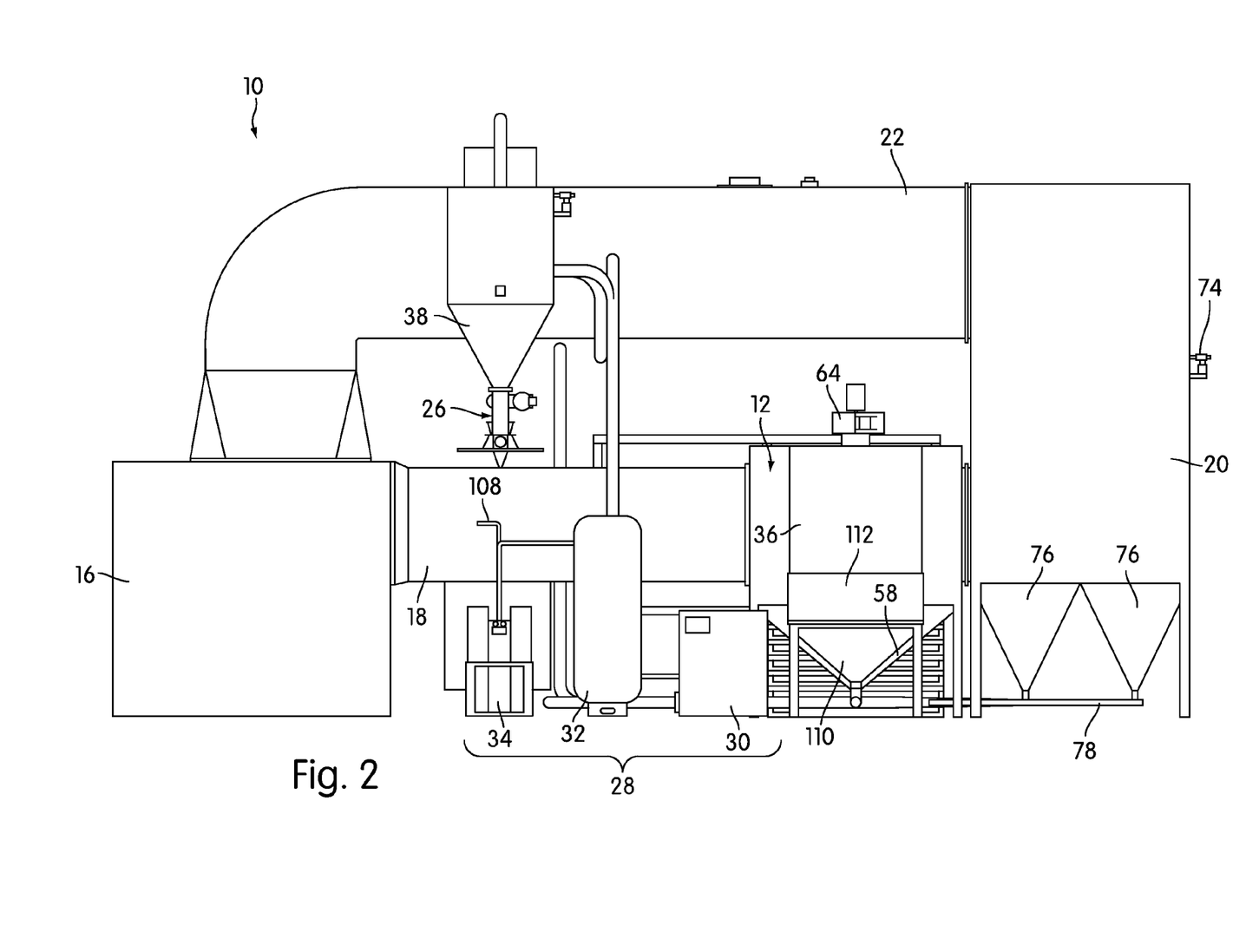
FIG. 2 is a rear elevational view of the testing system of FIG. 1.

FIG. 2 is a rear elevational view of the testing system 10. In addition to the air handling system 14, the testing system 10 includes a particulate delivery system 26, which feeds precisely defined amounts of sand or dust into the delivery duct 18. A compressed air system 28, including a compressor 30, a compressed air tank 32, and an air dryer 34, is used by the particulate delivery system 26 and by certain other systems, as will be described below in more detail. A particulate material handling system, including a material input station 36, a feed hopper 38, and a waste hopper 40 (shown in FIG. 1) connected by appropriate piping, is used to introduce sand or dust into the system 10, move the sand or dust into position to be injected into the delivery duct 18 by the particulate delivery system 26, and move the sand or dust out of the system 10 after use.

The overall process of a test is controlled by a computing system 42, which, in the illustrated embodiment, comprises a programmable logic controller (PLC), such as an Allen-Bradley PLC. In other embodiments, other types of computing systems may be used, including general purpose computers. In the illustrated embodiment, the interface with the computing system 42 is by means of a touch screen display 44 (shown in FIG. 1), although keyboards, mice, and other conventional input/output devices may be used.

Air Handling and Flow

Figure 3:
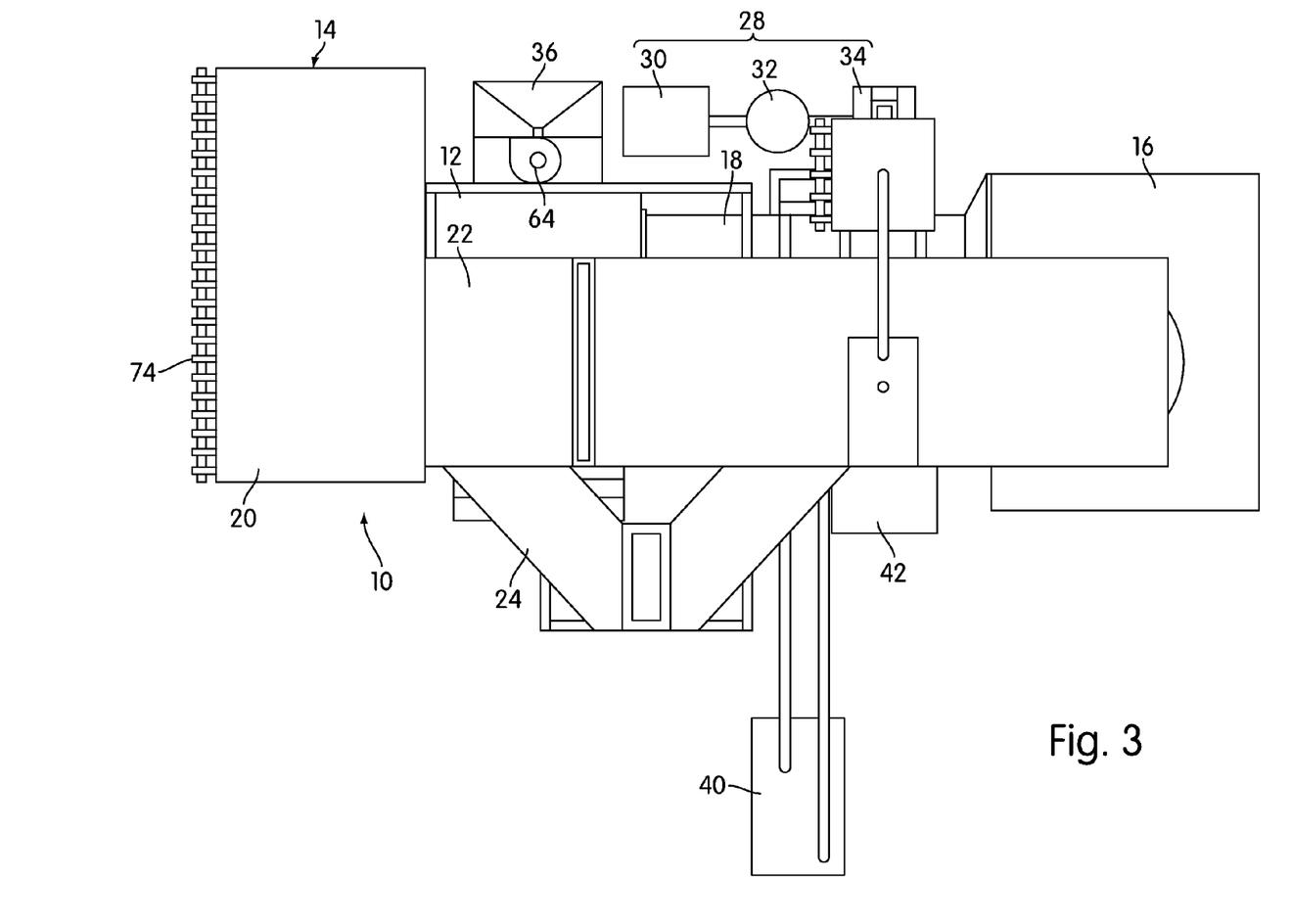
FIG. 3 is a top plan view of the testing system of FIG. 1.
Figure 4:
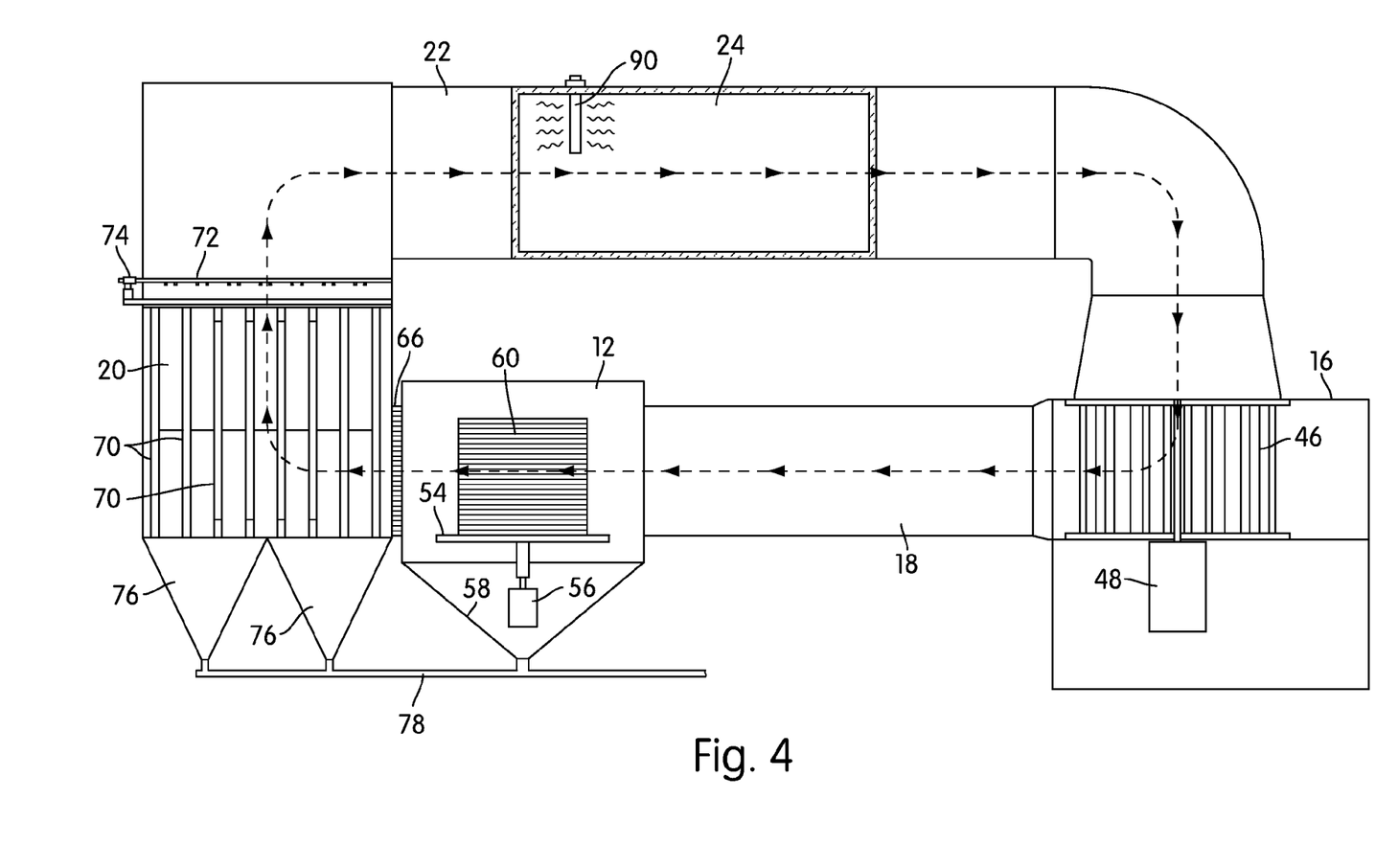
FIG. 4 is a simplified, schematic front elevational view of the testing system of FIG. 1 in partial cross-section, illustrating the main airflow within the system during a test.

FIG. 3 is a top plan view of the testing system 10, and FIG. 4 is a simplified schematic view of the airflow through the system. As shown in FIG. 4, air flows in a basic loop around the system, and is recirculated throughout a typical test. The airflow loop begins at the air mover or blower 46, which is mounted horizontally for rotation along a vertical axis of rotation within the blower housing 16.

The blower 46 may be any type of blower or air mover capable of producing the airspeeds and volumes used in a sand or dust environmental test, and depending on the type of blower, it may be mounted vertically or horizontally. The blower wheel or fan itself may be made of any suitable material, although it may be advantageous if the blower wheel is made of a non-sparking material, such as aluminum. The blower 46 of the illustrated embodiment is driven by a motor 48. It is advantageous if the motor 48 is capable of variable speeds, so that the blower 46 may be driven to move air at speeds between, for example, 1500 feet per minute (FPM) (17.3 miles per hour (MPH)) and 5777 FPM (65.6 MPH). The motor 48 may have, for example, a rated power of 150 horsepower and may include its own cooling system, such as a fan cooling system, and other conventional subsystems not shown in FIG. 4.

Although portions of this description may refer to a single main blower, embodiments of the invention may use more than one blower, arranged either in series or in parallel, in order to create the necessary air flow. With multiple blowers, each of the individual blowers may be considerably smaller than a blower 46 of comparable capabilities. For that reason, multiple blowers may be particularly useful in situations in which the physical space available for system 10 is limited. As those of skill in the art will realize, placing blowers in parallel increases the volume of air flow in the system; placing them in series does not change the volume but does increase the pressure. If used, multiple blowers could be co-located in a single housing, or individual blowers could be located in different locations around the airflow loop. However, as will be described below in more detail, it is advantageous if the blower 46 or blowers are on the "clean" side of the airflow loop.

The blower housing 16 may be sound insulated with appropriate thicknesses of soundproofing materials so as to reduce ambient noise from the blower 46. Additionally, the blower housing 16 and all other elements of the testing system 10 would generally be thermally insulated in order to maintain the airflow at the temperatures desired for an environmental test.

As will be described below in more detail, in the testing system 10, the blower 46 is on the "clean" side of the airflow loop. In other words, air with entrained sand or dust does not pass through the blower 46. This may reduce wear and tear on the blower 46. Additionally, it may be a significant advantage over environmental testing systems in which air with entrained sand or dust does pass through the blower. Without intending to be bound by any particular theory, it is believed that abrasive sand passing through a conventionally-arranged blower may wear the blower and shorten its lifetime. The wear may also alter the surface area of a conventionally-arranged blower's blades, thus decreasing the flow and velocity of the air and entrained particulate matter. Conventional systems may or may not be able to register and compensate for these blower erosion problems, thus leading to inaccurate test results and repeatability problems. By contrast, the arrangement shown in FIG. 4 avoids these problems.

From the blower housing 16, the airflow passes into and through the delivery duct 18. The delivery duct 18 is generally rectangular in shape and interior cross-sectional area, and is the portion of the air handling system 14 where particulate matter, in this case either sand or dust, is introduced into the airflow. In some embodiments, the delivery duct 18 may include static neutralizing vanes upstream of the point at which the sand or dust is introduced. Alternatively, these static neutralizing vanes may be arranged at or near the exit to the blower housing 16. These static neutralizing vanes would be connected to the compressed air system 28 and would use compressed air and appropriate electrical circuitry to create a stream of ionized airflow that tends to reduce or eliminate static electricity.

From the delivery duct 18, the airflow passes into the environmental test chamber 12 itself. The environmental test chamber 12 would typically have sufficient dimensions such that a piece of equipment of considerable size can be tested. For example, in one embodiment, the environmental test chamber may be six feet high, six feet wide, and eight feet long. It may be constructed of a metal, such as steel or aluminum, insulated along the exterior with thermal insulation, such as glass fiber insulation. A hinged door 50 with a clear, transparent window 52 for viewing is hingedly attached to the front of the environmental test chamber 12. In some embodiments, a static neutralizing system may be provided on the interior of the door 50 proximate to the window 52, in order to prevent the window 52 from being obscured by statically-adhered sand or dust during a test. The environmental test chamber 12 may also have an interior lighting system to facilitate viewing of the test piece during a test.

The environmental test chamber 12 will typically include some kind of support 54 on which a test piece is to be placed for testing. In one embodiment, that support may be, for example, a 54-inch by 54-inch steel grate table capable of supporting up to 2,000 total pounds of weight. Although solid tables and supports may be used, the use of grate tables or tables with other types of openings allow sand and dust to fall downwardly, through the support 54, once the particles have impacted the test piece. In other embodiments, the support 54 may be round or of any other suitable shape.

The support 54 may optionally be mounted on a motor 56 for rotation, so that the test piece can be rotated during the test without having to pause the test and open the door 50 to the environmental test chamber 12. The rotation of the support 54 would generally be under the control of the computing system 42. Depending on the nature of the test, the support 54 may be directed to rotate continuously in 360° circles, or the computing system 42 may be programmed to rotate the support 54 in increments over specific time intervals during the test. In some embodiments, the motor 56 may be controlled simply by turning its power supply on and off. In other embodiments, the motor 56 may be a stepper motor or another type of motor that can be directly electrically addressed and controlled. Most embodiments of the invention will include either a motor 56 capable of recording and communicating the angular position of its shaft to the computing system 42, or alternatively, a separate angular position sensor on the shaft on which the support 54 is mounted.

The presence of a rotatable support 54, although optional, provides certain advantages. With such a rotatable support 54, users can investigate not only the overall effect of sand, dust, and temperature on a test piece, but also the effects of changing the angle of attack of the sand and dust. For example, by rotating the test piece, users can establish whether a particular part, side, or aspect of the test piece wears or reacts more strongly to the environmental conditions than other parts. If the angular position of the support 54 is monitored and recorded, the user can more easily determine whether a failure of a particular side or aspect of a test piece is repeatable.

As shown in FIG. 4, the bottom 58 of the environmental test chamber 12 has the general shape of an inverted pyramid, which allows any particles that may fall toward the bottom of the chamber 12 to be collected in a manner that will be described below in more detail.

At the rear of the environmental test chamber 12, an air outlet and a series of louvers 60 covering the air outlet are provided. The louvers 60 are controlled by the computing system 42 that controls the testing system 10 and provide a pathway for air to move out of the environmental test chamber 12 and the testing system 10. That pathway is used, and the louvers 60 are opened, for a number of different reasons.

As can be appreciated from the rear elevational view of FIG. 2, the back of the chamber 12 where the louvers 60 are located abuts and shares a wall with the material input station 36. The interior of the material input station 36 contains a number of canister-type filters 62 (best seen in the view of FIG. 7), which lie upstream of an exhaust fan 64 at the top of the material input station 36. Just upstream of the exhaust fan 64 is a secondary filter element, such as a high efficiency particulate air (HEPA) filter (not shown in the figures). Therefore, when the louvers 60 on the back wall of the environmental test chamber 12 are open, it creates an airflow pathway through the canister filters 62 of the material input station 36, through the secondary filter, and out to the surrounding air through the exhaust fan 64. The exhaust fan 64 is generally much smaller than the main blower 46, but should be sized to create a substantial draw, such as a 200 FPM draw. The canister filters 62 and secondary filter may filter the escaping air to, for example, 99.96% at 2.5 micron size. As those of skill in the art will realize, the particular types of the filters are not critical, so long as they are suitable for the application.

The airflow pathway created by the interaction of the louvers 60 and the material input station 36 can be used for two main purposes. First, the door 50 to the environmental test chamber 12 may be equipped with an electrical switch, such that its opening can be detected. When the door 50 is opened, the louvers 60 are opened and the exhaust fan 64 started, creating a negative pressure draw within the environmental test chamber 12. This negative pressure draw is used to protect the operator —any sand or dust that may be in the chamber 12 when the door 50 is opened is drawn out and away from the operator and is filtered before being exhausted. This may be of particular use at the end of a test, when there may be a substantial accumulation of particulate matter in the chamber 12. Of course, the exhaust fan 64 may also be manually activated by a separate switch or through the interface 44 of the computing system 42.

Additionally, the louvers 60 may be opened and the exhaust fan 64 triggered during a test in order to draw air out of the airflow loop. This can be used, for example, to compensate for the expansion of the air within the system 10 as the air is heated.

In some embodiments, there may be certain advantageous relationships between the sizes and cross-sectional areas of certain components of the testing system 10. For example, the cross-sectional area of the delivery duct 18 and its outlet may be determined such that when there is a test piece of maximum testable cross-sectional area in the environmental test chamber 12, there is no reduction in the overall area through which air is permitted to flow, and thus, no slowing of the incoming air. Moreover, typically, the airflow exitway 66 from the environmental test chamber 12 would have the same cross-sectional area as the delivery duct 18 and its inlet, so that there is no backpressure that might otherwise be caused by a change or restriction in the airflow path.

From the airflow exitway 66 leading from the environmental test chamber 12, air moves into the filter chamber 20, where any remaining particulate matter is stripped from the airflow. The upper portion of the filter chamber 20 is filled with a number of filter elements 70, which may be, for example, cylindrical "bags" constructed of a conventional filtration material, such as polyester felt. These filter elements 70 may be mounted on or suspended from a rack or racks 72. The rack or racks 72 may themselves be connected to agitator levers or knobs 74 that can be actuated to agitate the racks 72 and the filter elements 70 that are suspended from them. Agitation of the filter elements 70 may clean them by causing particulate matter encrusted on them to drop to the floor of the filter chamber 20. In some embodiments, the compressed air system 28 may be connected to the filter chamber 20 such that it can deliver bursts of compressed air to the filter elements 70 to clean them.

In addition to filter elements 70, mechanical obstructions, baffles, and tortuous airflow pathways may be used to separate air from entrained particulate matter. For example, in some embodiments, a baffle or baffles may be located in the airflow exitway 66 or the filter chamber 20 to facilitate separation. Of course, as noted above, it is preferable if the baffles are sized and arranged such that they do not create backpressure within the environmental test chamber 12.

The bottom of the filter chamber 20 comprises a pair of bottom spaces 76 that have the general shape of inverted pyramids, similar to the bottom 58 of the environmental test chamber 12. Like the bottom 58 of the environmental test chamber 12, the bottom spaces 76 allow captured particulate matter to be collected.

As shown in FIG. 4, the bottom 58 of the environmental test chamber 12 and the bottom spaces 76 of the filter chamber 20 are connected to a common set of piping 78 that allows collected particulate material to be pneumatically or otherwise conveyed elsewhere.

At the top of the system 10 and the top of the airflow loop are the upper ducts 22, 24 that direct the air back toward the blower housing 16 and contain the temperature control system. The arrangement of the two ducts 22, 24 is best seen in the top plan view of FIG. 3, and can also be seen in FIG. 5, which is a top cross-sectional view of the ducts 22, 24.

Figure 5:
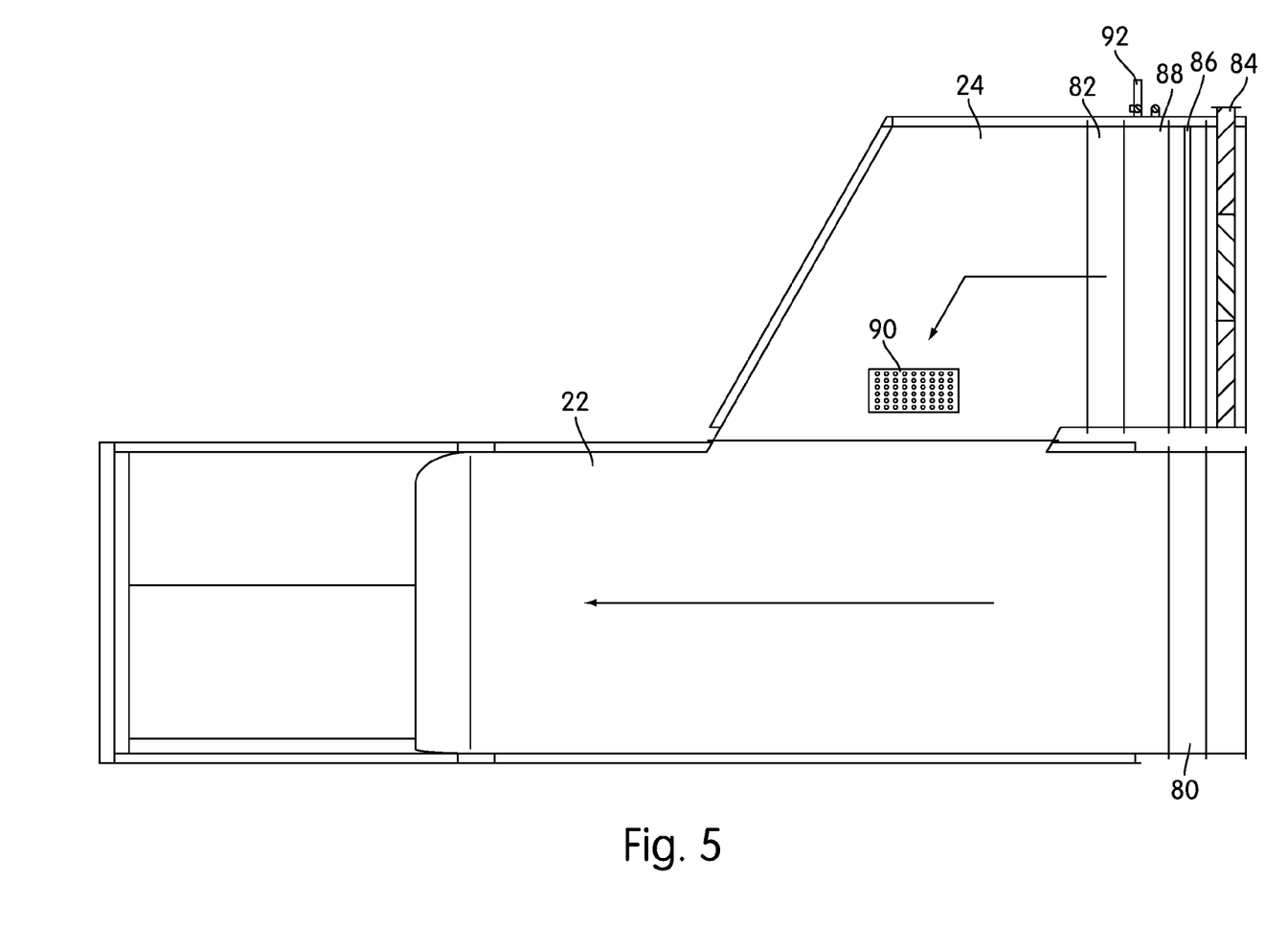
FIG. 5 is a cross-sectional view of the upper ducts of the testing system of FIG. 1, illustrating the heating and cooling mechanisms.

Air normally flows through the main duct 22. However, a set of dampers 80, 82 linked to the computing system 42 allows the flow to be directed either into the main duct 22 or into the heating and cooling duct 24. Prior to the damper 82, the heating and cooling duct 24 includes a filtering element 84, such as a fibrous filter, and a cooling element 88. Provided between the filtering element 84 and the cooling element 88 is an air velocity sensor 86. Downstream from those elements in the heating and cooling duct 24 is a heating element 90, such as a resistive heating element. In some embodiments, only a single damper 80, 82 may be provided.

As was explained above, sand and dust environmental tests are typically run at an elevated temperature. Typically, at the beginning of a test, the computing system 42 would power on the heating element 90, close the damper 80 in the main duct 22, and open the damper 82 in the heating and cooling duct 24, thus forcing the airflow through the heating and cooling duct 24. As it circulates through the heating and cooling duct 24, the airflow would be heated until it reaches a setpoint temperature, e.g. 170° F. (77° C.), at which point the heating element 90 would be shut off and the air rerouted through the main duct 22.

During the test, the temperature of the air will typically rise by a degree or two each time it passes through the blower 46, because of heat transfer and friction. Therefore, once the air in the system has reached an initial temperature setpoint, it may not be necessary to keep the heating element 90 on during the major portion of a test. Generally speaking, adequate thermal insulation in the air handling system 14 and other components will be sufficient to maintain air temperature at a desired setpoint. However, in situations in which the setpoint is particularly high or in which portions of the air handling system 14 cannot be well insulated, the heating element 90 may be turned on during the test and the dampers 80, 82 may direct at least a portion of the airflow through it.

At various times, it may be desirable to cool the air circulating through the system 10 in order to maintain a desired setpoint temperature and avoid temperature overshoot. For that reason, the damper 82 can be opened, the damper 80 in the main duct 22 can be closed, and the cooling element 88 activated. Depending on the embodiment, the cooling element 88 may comprise a refrigerant-driven cooling system, a heat exchanger, one or more thermoelectric cooling elements, a set of tubing through which chilled water flows, or any other conventional cooling mechanism. A pipe 92 or set of pipes may be used to convey chemical refrigerant, chilled water, or other elements into and out of the cooling element 88, if necessary.

Of course, the act of actively heating and cooling the air in the system 10 also has the effect of drying it, as moisture is forced to condense on the cooling element 88. For that reason, in some embodiments, a drip pan and appropriate piping may be used to convey condensed water out of the system.

Because of their drying effects, the cooling and heating elements 88, 90 may be used to maintain a desired or required level of humidity in the airflow. In some embodiments, even if a test is conducted at room temperature, the cooling and heating elements 88, 90 may be activated so that their effects will dry the air within the system. In other embodiments, a separate, conventional desiccant-based system may be used to dry the entire airflow within the system, although using the heating and cooling system for drying is generally advantageous.

In the description above, it should be understood that although the dampers 80, 82 are referred to as being in either open or closed states, the dampers 80, 82 could be placed in partially open or partially closed positions, such that some of the airflow would flow through the heating and cooling duct 24.

Additionally, although in the illustrated embodiment, both heating and cooling elements are provided in the heating and cooling duct 24, in some embodiments, one element may be provided in each duct 22, 24, with the dampers 80, 82 used to control where the air flows depending on whether it requires heating or cooling.

Sand and Dust Delivery

Generally, tests using the testing system 10 will use either sand or dust in a single test. As was noted above, the system 10 provides a particulate delivery system 26 capable of delivering a metered amount of sand or dust per unit time or airflow volume into the delivery duct 18 in such a way that the particulate matter injected into the delivery duct 18 is evenly distributed and of uniform velocity by the time it enters the test chamber. The uniform velocity with which the particulate matter is injected will typically at least substantially match the velocity of the surrounding airflow. In this description, the term "particulate matter" is used to refer to either sand or dust. In most embodiments, the testing system 10 will handle sand and dust in essentially the same way during a test, with the exception that dust is typically recycled through the system 10, while sand is not. Of course, in some embodiments, sand may be recycled during a test. Ultimately, however, it should be understood that systems according to embodiments of the invention may deliver any form of particulate matter.

A fluidized mixture of air and particulate matter is pneumatically conveyed to a separator 94, which includes its own set of filtration elements 96. The separator 94 sits atop the feed hopper 38, such that when the fluidized air/particulate matter mixture enters the separator 94, the particulate matter is forced out of the airflow by filtration elements 96 and drops down into the feed hopper 38. (The air in which the particulate matter was entrained is recycled through the system 10.) The filtration elements 96 are similar to others in the testing system 10 (although they may be smaller and less numerous), and are mounted on their own rack 98, which is connected to an agitation mechanism 100 for filter cleaning. As was noted briefly above, the compressed air system 28 may also be connected to the separator 94 to pulse the filtration elements 96 and thus remove the particulate matter from them. Additionally, as was also noted above, mechanical baffles and tortuous airflow pathways may also be used to facilitate separation.

A feeder mechanism 102 coupled to the feed hopper 38 feeds metered amounts of particulate matter into an injector 104 which injects the particulate matter into the airflow within the delivery duct 18. The feeder mechanism 102 may, for example, be a loss-in-weight gravimetric feeder, or any other type of feed mechanism capable of feeding a specified unit volume or weight of material in a specified unit of time. One example of such a feed mechanism is the ROTARY SCALPEL™ feeder mechanism sold by 3I's Technologies, Inc. (Vineland, N.J., United States).

Several different types of injectors 104 may be used in embodiments of the present invention. In general, injectors fall into two categories: (1) eductor-type injectors that have separate inlets for the material to be delivered and for the motive gas or force; and (2) single inlet and outlet injectors. For example, a Venturi valve, one suitable type of injector 104, falls into the first category. Injectors that fall into the second category, such as blast pots regulated by appropriate valves, typically have a charged or pressurized reservoir from which the material is fed.

Figure 6:
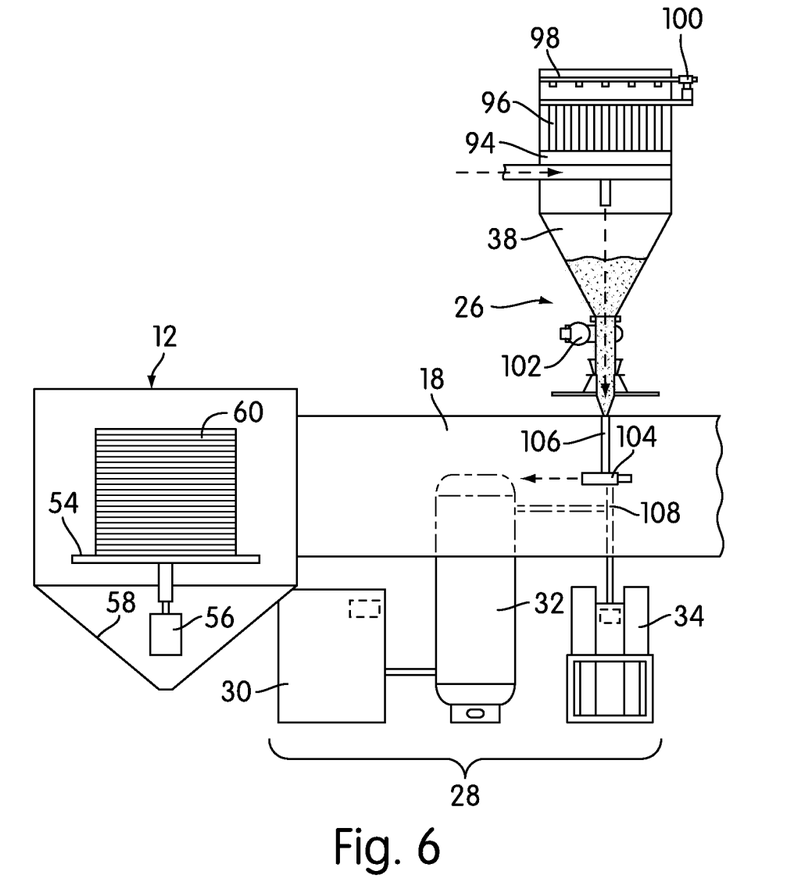
FIG. 6 is an elevational view of the particulate injection mechanism of the testing system of FIG. 1 in isolation.

The injector 104 in the illustrated embodiment is a Venturi valve. As shown in the view of FIG. 6, the injector 104 is connected to the feeder mechanism 102 and is mounted on a pipe or tube 106 that places the injector 104 in the center of the delivery duct 18. The Venturi valve is actuated by the compressed air system 28; specifically, compressed air flows from the air dryer 34, which would typically be desiccant-based, through a pipe 108 that enters the side of the delivery duct 18 and is connected to the injector 104. The compressor 30 and air tank 32 ensure that the testing system 10 maintains a reserve of compressed air sufficient to actuate the Venturi valve injector 104 continuously throughout the duration of a typical test. The compressed air system 28 may deliver, for example, sixty CFM of compressed air at eighty pounds per square inch (psi) in order to actuate the Venturi valve injector 104. The pressure that the compressed air system 28 delivers may be regulated and varied to vary the velocity of the particulate matter.

Although portions of this description refer to compressed air and a compressed air system, depending on the nature and type of injector 104 and the nature of the test that is to be performed, other types of gases may be used to provide motive force for injecting particulate matter. For example, in some embodiments, a light, inert gas, such as nitrogen, may be used instead of compressed air.

The injector 104 injects the particulate matter into the delivery duct 18 such that the particulate matter entering the delivery duct 18 has a velocity that at least approximately matches the velocity of the surrounding airflow. The position of the injector 104 in the delivery duct may be defined by regulatory requirements, and in particular, it may be located a defined horizontal distance (e.g., ten feet) from the entrance to the chamber 12.

Regulatory requirements that define the distance between the point of particulate matter introduction and the chamber 12 are typically intended to ensure uniform distribution and velocity of the particulate matter as it enters the chamber 12. However, because the injector 104 injects a precise amount of particulate matter into the airflow at approximately the same velocity as the surrounding airflow, testing systems 10 according to embodiments of the invention may be able to achieve uniform particulate distribution and velocity with far less distance between the injector 104 and the chamber 12. Testing systems 10 according to embodiments of the invention may also be able to achieve laminar flow more readily than prior art systems. Moreover, the presence of the particulate matter in the airflow may make it possible in at least some cases to visually verify the existence of laminar flow entering the chamber 12 by looking through the window 52.

Additionally, because the injector 104 is positioned in the center of the delivery duct 18, rather than at the top or along one of the sides, it may be easier for the particulate matter to reach a uniform spatial distribution in the airflow.

Another advantage of the particulate delivery system 26, and the system 10 as a whole, is that by feeding a measured quantity of particulate matter into the delivery duct in a defined unit of time, the particulate delivery system 26 makes it possible to calculate the concentration of particulate matter in the airflow at any given time. In some embodiments, the computing system 42, which may actively control the particulate delivery system 26 or take input from its sensors, would make these concentration calculations automatically and in real time during a test.

Particulate Matter Conveying System

As was described briefly above, particulate matter is conveyed pneumatically in fluidized form through the system 10. Overall, a pneumatic conveying system is gated or valved so that the same pneumatic components can be used to convey material either into or out of the system 10.

The following description focuses on the arrangement and components of the pneumatic conveying system. However, as those of skill in the art will realize, in other embodiments, other methods may be used to convey material through the system, including screw-driven conveyors and aero-mechanical conveyors. As one example of an alternative conveying system, aero-mechanical conveyors that use a series of cable-connected disks within a pipe or tube, such as those sold by AEROCON (Belleville, N.J., United States), may be used to convey material.

With respect to the illustrated embodiment, particulate matter enters the system 10 through the material input station 36, which is located in the rear of the system 10, directly behind the chamber 12. As shown in the elevational view of FIG. 2, the material input station 36 has a reservoir 110 which is covered by a hinged cover 112. In order to introduce particulate matter into the system 10, a user lifts the cover 112 and deposits the particulate matter into the reservoir 110.

As with other elements of the system 10, the material input station 36 includes user protection features that help to prevent user exposure to and inhalation of particulate matter. Specifically, the hinged cover 112 is coupled to a switch, such that when the cover is lifted, the exhaust fan 64 located at the top of the material input station 36 is activated. The activated exhaust fan 64 draws air upwardly, through the filter elements 62, creating a negative pressure within the material input station 36 and drawing any particulate matter that may get into the air away from the user. Of course, an external switch could be provided to activate the fan 64, or it could be activated through the interface 44 of the computing system.

Figure 7:
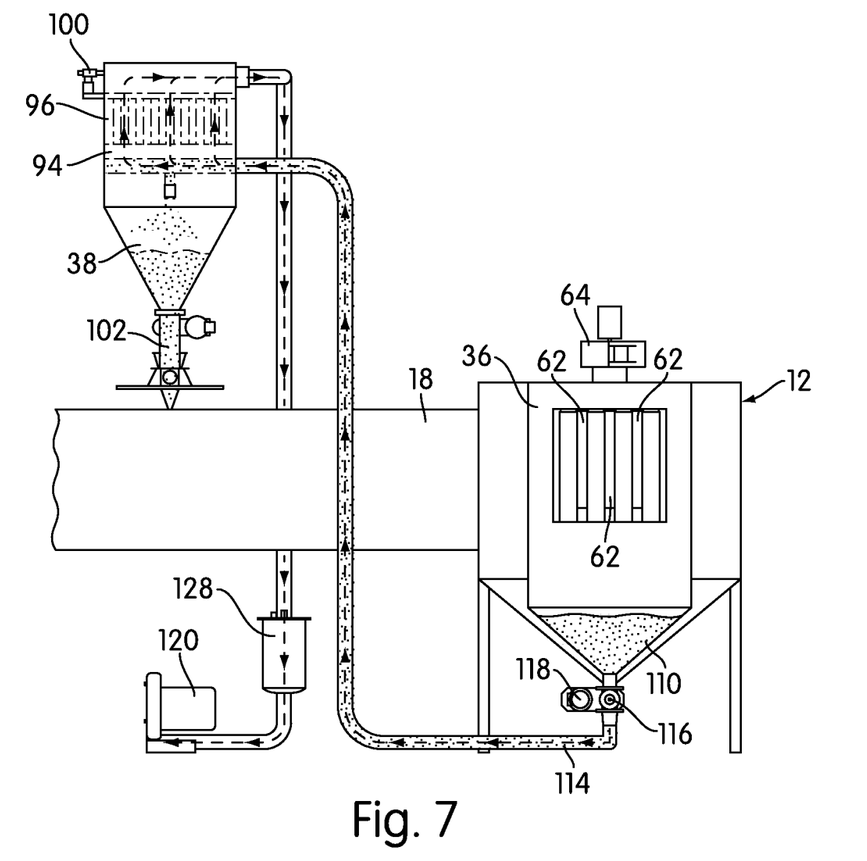
FIG. 7 is an elevational view of the particulate loading mechanism of the testing system of FIG. 1 in partial section, showing how particulate matter is conveyed.

FIG. 7 is an elevational view of the material input station 36, separator 94, and feed hopper 38, with the material input station 36 in partial section. A pipe 114 leads from the reservoir 110 to the separator 94 above the feed hopper 38. Located between the reservoir 110 and the pipe 114 and in communication with both are a rotary valve feeder 116 and an air inlet 118. As the feeder 116 gradually feeds the particulate matter from the reservoir 110 into the pipe 114, a pump 120 placed in fluid communication with the pipe 114 draws air into the system through the air inlet 118. The incoming air fluidizes the particulate matter and allows it to be conveyed through the pipe 114 to the separator 94.

Figure 8:
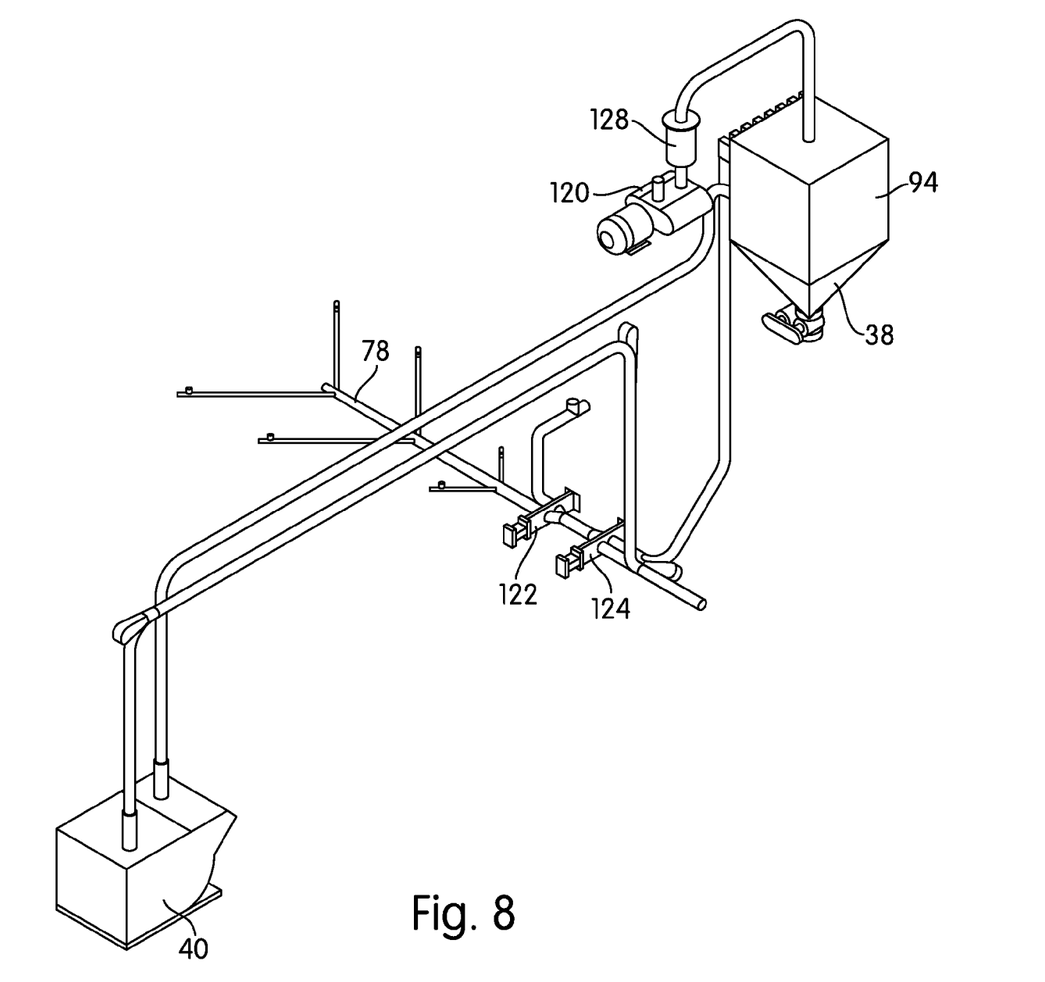
FIG. 8 is a perspective view of particular components of a pneumatic conveying system for sand and dust, shown in isolation.

Much of the rest of the pneumatic conveying system can be seen in the perspective view of FIG. 8, which shows the pneumatic conveying system in isolation. Once the particulate matter has been injected into the delivery duct 18 and brought through the chamber 12, it is collected from the bottom 58 of the chamber 12 and the bottom spaces 76 of the filter chamber 20 by a set of collection pipes 78, as was noted briefly above.

A set of gates 122, 124 direct the flow of the fluidized particulate matter. As was described above, dust is often recirculated throughout the duration of a single test, while sand typically is not recirculated. Therefore, dust is typically directed from the collecting pipes 78 back to the separator 94, where it is ultimately fed into the feed hopper 38 and re-introduced into the delivery duct 18.

Once a dust test is complete, or after sand is collected in the collection pipes 78, it is conveyed to the waste hopper 40. The waste hopper 40 includes an internal knockdown chamber that removes the particulate matter from the fluidized stream by impingement on a plate or baffle. The air is then routed from the waste hopper 40 back into the system 10. The waste hopper 40 itself may be located outside of a building in which the rest of the testing system 10 is located, and is arranged to be "self-dumping," such that material in the waste hopper 40 can be easily loaded onto a truck or other conveyance for disposal.

In addition to the various filtration and separation elements employed by the testing system 10, the pump 120 has a secondary or safety filter element 128 associated with it. The purpose of the safety filter element 128 is to protect the pump 120 from damage in the event that air reaching and passing through the pump 120 is insufficiently filtered.

Methods of Operation and Testing

FIG. 9 is a flow diagram of a method, generally indicated at 200, of operating the environmental testing system 10 to conduct sand and dust environmental tests. Method 200 begins at 202, typically with the user loading the test piece into the chamber 12, and continues with task 204.

In task 204, the user enters basic test data into the computing system 42, usually including the type of test that is to be conducted (sand or dust), the desired air velocity (e.g., in units of feet or meters per minute), and the desired particulate matter concentration. From those basic inputs, the particulate delivery system 26 calculates the weight of particulate matter per unit of time that is to be injected (e.g., pounds or kilograms per hour). In some embodiments, rather than entering specific numerical setpoints for air velocity and particulate matter concentration, the user may be permitted to select from a pre-programmed list of testing options and protocols.

Method 200 continues with task 206. In task 206, the blower 46 is turned on and set to move with an initial velocity (e.g., 10 Hz) in order to circulate air within the system 10 for heating. Next, in task 208, the pneumatic gates 122, 124 are set for loading particulate matter into the system 10, and the user is prompted to load particulate matter.

The user then loads the particulate matter into the material input station 36. As shown in task 210 of method 200. As described above, while particulate matter is being loaded, the exhaust fan 64 is activated to draw any airborne matter away from the user. Once material is loaded, method 200 continues with task 212.

Task 212 of method 200 begins the process of bringing the temperature and humidity of the system to the desired or specified conditions for testing. In particular, task 212 is a decision task. If the air temperature and humidity are not at the desired setpoints (task 212:NO), the heating element 90 is turned on and/or maintained in operation in task 214. If the temperature and humidity have reached their desired setpoints (task 212:YES), method 200 continues with task 216.

In task 216, if necessary, the pneumatic gates 122, 124 and other elements are set to the settings that are to be used for the test. Next, in task 218, the blower 46 is ramped up to the velocity needed for the test.

After task 218, the environmental testing system 10 is ready to conduct a test. At that point, method 200 may pause until a user provides a command or pushes a button to begin a test. Once the user initiates the test, method 200 continues with task 220, in which the particulate delivery system 26 begins to feed the particulate matter into the delivery duct 18.

Once the test has begun, method 200 begins an iterative loop to monitor temperature, humidity, air flow, and blower speed. More particularly, task 222 is a decision task in which the computing system 42 checks to see whether the temperature is greater than the desired setpoint. In some cases, a threshold may be used, so that the actual determination is whether the temperature is greater than the setpoint plus the threshold. For example, in one embodiment, the threshold may be about three degrees. If the temperature is greater than the setpoint or the setpoint plus the threshold (task 222:YES), method 200 continues with task 224, the cooling element 88 is activated, and the appropriate dampers 80, 82 are actuated so that air flows into the heating and cooling duct 24. If the temperature is not greater than the setpoint or the setpoint plus the threshold (task 222:NO), method 200 continues with task 226. As an additional consequence of task 222, if the dampers 80, 82 were previously actuated to move air into the heating and cooling duct 24, they may be actuated to move air through the main duct 22.

Figure 9:
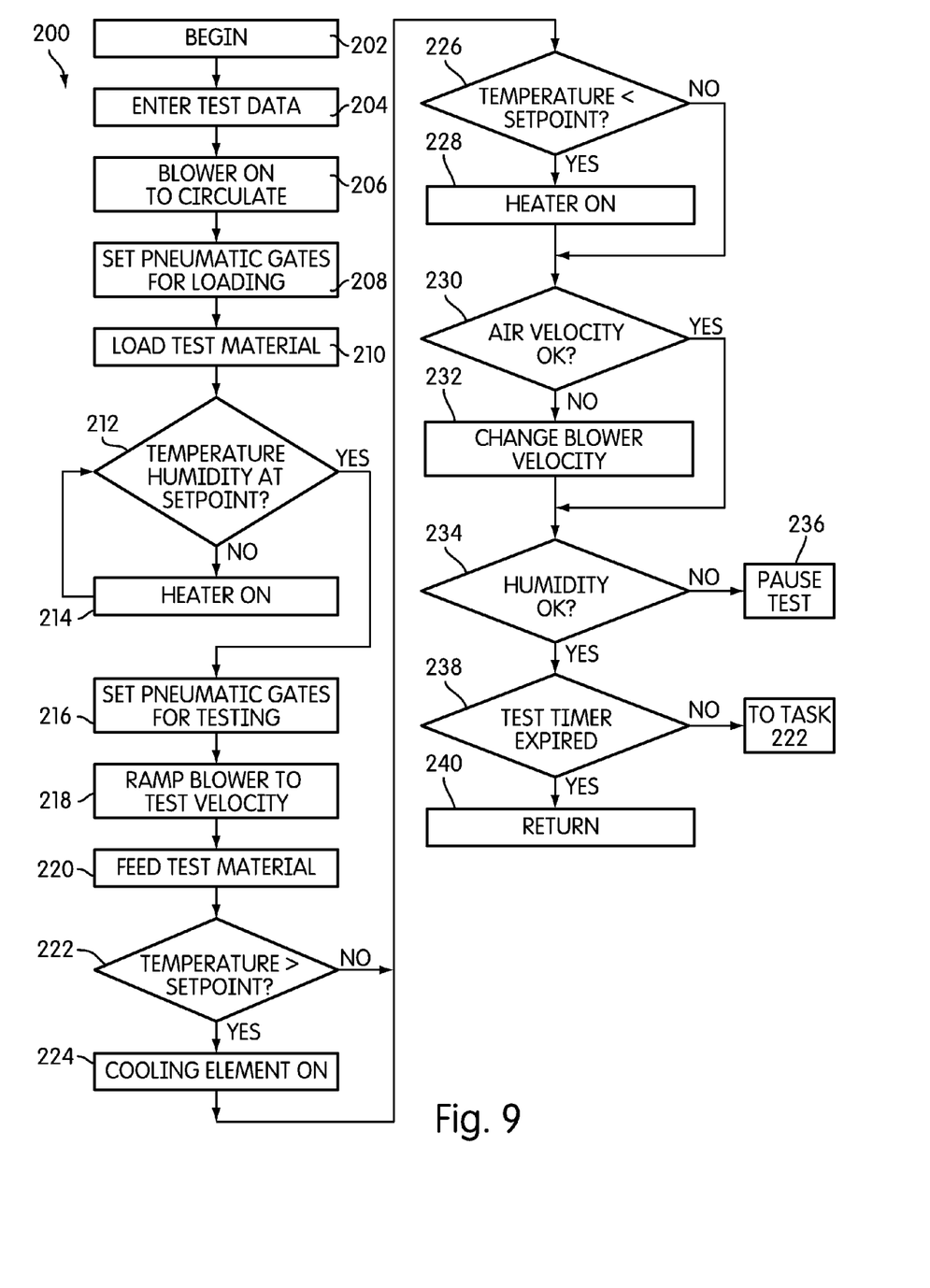
FIG. 9 is a flow diagram of the tasks involved in conducting a sand or dust environmental test using the testing system of FIG. 1.

In task 226, the computing system 42 determines whether the air is too cold. More specifically, in task 226, the air temperature is checked against the setpoint. If the temperature is less than the setpoint, or less than the setpoint plus a threshold (task 226:YES), then method 200 continues with task 228, the heating element 90 is activated, and the appropriate dampers 80, 82 are actuated so that air flows into the heating and cooling duct 24. If the temperature is not less than the setpoint, or less than the setpoint plus a threshold, method 200 continues with task 230. As an additional consequence of task 222, if the dampers 80, 82 were previously actuated to move air into the heating and cooling duct 24, they may be actuated to move air through the main duct 22.

In task 230, the output of a sensor, such as a differential pressure sensor or anemometer, is checked to determine whether the air velocity is within defined limits for the test. If the air velocity is not within the defined limits or does not meet a setpoint (task 230:NO), then method 200 continues with task 232, in which the blower speed is adjusted up or down to bring the air velocity to the desired setpoint or within the defined limits. If the air velocity is within the defined limits and/or meets the appropriate setpoint (task 230:YES), method 200 continues with task 234. In some embodiments, the rotational speed of the blower 46 may also be noted and recorded. Checking the air velocity and adjusting the blower speed if necessary during the test ensures that the system can compensate for variations in the performance of the blower 46. Data that correlates blower speed with air velocity can also be used to adapt an existing test standard or create a new one.

In task 234, the computing system 42 determines whether the humidity in the system is appropriate. If the humidity levels are not within defined limits (task 234:NO), the computing system 42 may pause the test, stop the feeding of particulate matter, and wait for conditions to change, as shown in task 236, or may stop the test entirely. Pausing the test may not be necessary in all embodiments; however, if the humidity is outside of the specified ranges, the particulate matter may clump up or otherwise become non-uniform in its distribution. If the humidity is within defined limits (task 234:YES), method 200 continues with task 238.

In task 238, the computing system 42 checks to see whether the test timer has expired. If the test timer has expired and the test is therefore over (task 238:YES), method 200 completes and returns at 240. If the test timer has not expired, control of method 200 returns to task 222, and method 200 continues.

During the test, a number of other conditions may result in the test being paused or terminated early. For example, if the particulate delivery system 26 is not delivering particulate matter at the appropriate rate, the test may be paused or terminated.

Once the test is complete, the pneumatic gates 122, 124 may be set and the pump 120 activated to move the particulate matter to the waste hopper 40, if necessary. With sand, this would generally be done automatically during the test; with dust, it may be performed either automatically at the end of the test or manually after the test is complete.

While the invention has been described with respect to certain embodiments, the description is intended to be exemplary, rather than limiting. Modifications and changes may be made within the scope of the invention, which is defined by the appended claims.

What is claimed is:

1. An environmental testing system, comprising:
    an environmental test chamber having an interior volume into which a test piece can be placed for testing, the environmental test chamber having an inlet, an outlet, an openable door through which the interior volume can be accessed, and an openable air outlet;
    an inlet duct in communication with the inlet;
    a particulate matter feed mechanism coupled to the inlet duct, the particulate matter feed mechanism being constructed and arranged to feed particulate matter into the inlet duct for passage into the environmental test chamber;
    an outlet duct in communication with the outlet;
    a filter chamber in communication with the outlet duct, the filter chamber being provided with one or more filter elements constructed and arranged to remove particulate matter from air leaving the environmental test chamber through the outlet duct;
    a blower coupled between the filter chamber and the inlet duct such that an inlet of the blower is exposed to filtered air from the filter chamber, the blower being constructed and arranged to create an airflow within the environmental testing system;
    a particulate matter input hopper; and
    an operator protection system including:
        an exhaust fan, and
        one or more filtration elements in fluid communication with and upstream from the exhaust fan,
        wherein the exhaust fan and one or more filtration elements are in fluid communication with the openable air outlet of the environmental test chamber and the particulate matter input hopper so as to selectively create negative pressures within or around the environmental test chamber and the particulate matter input hopper.

2. The environmental testing system of claim 1, wherein the particulate matter feed mechanism comprises:
    an injector positioned within the inlet duct, the injector being constructed and arranged to inject particulate matter into the inlet duct with a velocity that at least substantially matches the velocity of a surrounding airflow in the inlet duct, and
    a feeder connected to the injector, the feeder being constructed and arranged to accept particulate matter from a feed hopper and feed the particulate matter in defined amounts into the injector.

3. The environmental testing system of claim 1, wherein the feeder comprises a loss-in-weight gravimetric feeder.

4. The environmental testing system of claim 1, wherein the injector comprises a Venturi valve.

5. The environmental testing system of claim 1, further comprising a particulate matter handling system including:
    a feed hopper;
    a waste hopper;
    a network of pipes connecting the particulate matter input hopper, the feed hopper, the waste hopper, the environmental test chamber, and the filter chamber;
    one or more valves or gates in the network of pipes; and
    a pump connected to the network of pipes;
    wherein the particulate matter handling system is constructed and arranged to (1) move fluidized particulate matter from the particulate matter input hopper to the feed hopper, (2) collect used particulate matter from the environmental test chamber and the filter chamber, and (3) direct used particulate matter back to the feed hopper or to the waste hopper.

\* \* \* \* \*

UNITED STATES PATENT AND TRADEMARK OFFICE
CERTIFICATE OF CORRECTION

PATENT NO. : 9,677,991 B2  
APPLICATION NO. : 14/253643  
DATED : June 13, 2017  
INVENTOR(S) : Daniel P. Lehman and Daniel A. Lehman Page 1 of 1

It is certified that error appears in the above-identified patent and that said Letters Patent is hereby corrected as shown below:

In the Claims

Column 14, Line 51, in Claim 3, please replace "The environmental testing system of claim 1, wherein the feeder comprises a loss-in-weight gravimetric feeder." with -- The environmental testing system of claim 2, wherein the feeder comprises a loss-in-weight gravimetric feeder. --.

Column 14, Line 53, in Claim 4, please replace "The environmental testing system of claim 1, wherein the injector comprises a Venturi valve." with -- The environmental testing system of claim 2, wherein the injector comprises a Venturi valve. --.

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*